United States Patent
Chen et al.

(10) Patent No.: US 12,011,303 B2
(45) Date of Patent: Jun. 18, 2024

(54) REAL-TIME PAIN DETECTION AND PAIN MANAGEMENT SYSTEM

(71) Applicant: CJSHINE TECHNOLOGY COMPANY LTD., Taipei (TW)

(72) Inventors: Lee-Kui Chen, Taipei (TW); Tzu-Kuei Shen, Taipei (TW)

(73) Assignee: CJSHINE TECHNOLOGY COMPANY LTD., Taipei (TW)

( * ) Notice: Subject to any disclaimer, the term of this patent is extended or adjusted under 35 U.S.C. 154(b) by 695 days.

(21) Appl. No.: 16/699,465

(22) Filed: Nov. 29, 2019

(65) Prior Publication Data
US 2020/0170581 A1    Jun. 4, 2020

Related U.S. Application Data

(60) Provisional application No. 62/894,532, filed on Aug. 30, 2019, provisional application No. 62/772,891, filed on Nov. 29, 2018.

(51) Int. Cl.
*A61B 5/00* (2006.01)
*A61B 5/024* (2006.01)
(Continued)

(52) U.S. Cl.
CPC ........ *A61B 5/7278* (2013.01); *A61B 5/02405* (2013.01); *A61B 5/349* (2021.01);
(Continued)

(58) Field of Classification Search
CPC ... A61B 5/7278; A61B 5/02405; A61B 5/349; A61B 5/4824; A61B 5/4839; A61B 5/7225; A61B 5/742; A61B 5/024; A61B 5/318; A61B 5/4005; A61B 5/7257; A61M 19/00; A61M 2230/04; G16H 20/13;
(Continued)

(56) References Cited

U.S. PATENT DOCUMENTS

| | | | |
|---|---|---|---|
| 2006/0217615 A1* | 9/2006 | Huiku | A61B 5/4821 600/484 |
| 2009/0229171 A9* | 9/2009 | Storm | C09K 5/18 44/250 |

(Continued)

FOREIGN PATENT DOCUMENTS

WO    WO-2009063463 A2 *    5/2009    ............... A61B 5/02

*Primary Examiner* — Michael R Bloch
(74) *Attorney, Agent, or Firm* — Birch, Stewart, Kolasch & Birch, LLP

(57) ABSTRACT

The present invention provides a system for real-time pain detection, which comprises a means for acquiring biomedical signals relating to pain in a subject in need thereof, a computing means for transforming the acquired biomedical signals during a given period of time into the signal data for measurement of pain, analyzing the data to divide into two or more models, including at least a pain model which is defined by the data showing a peak-shaped profile and a non-pain model which is defined by the data showing a flat profile, whereby the pain status of the subject is measured based on the results of the analysis, a process means for generating an index of pain using the results of the analysis depending on the subject's demands or sensation, and a display showing the pain status of the subject.

9 Claims, 14 Drawing Sheets
(12 of 14 Drawing Sheet(s) Filed in Color)

(51) Int. Cl.
*A61B 5/349* (2021.01)
*A61M 19/00* (2006.01)
*G16H 20/13* (2018.01)
*G16H 20/17* (2018.01)
*G16H 40/67* (2018.01)
*A61N 1/36* (2006.01)

(52) U.S. Cl.
CPC .......... *A61B 5/4356* (2013.01); *A61B 5/4824* (2013.01); *A61B 5/4839* (2013.01); *A61B 5/7225* (2013.01); *A61B 5/742* (2013.01); *A61M 19/00* (2013.01); *G16H 20/13* (2018.01); *G16H 20/17* (2018.01); *G16H 40/67* (2018.01); *A61N 1/36021* (2013.01); *A61N 1/36031* (2017.08)

(58) Field of Classification Search
CPC ........ G16H 20/17; G16H 40/67; G16H 20/10; G16H 50/20; G16H 50/50; A61N 1/36021; A61N 1/36031
See application file for complete search history.

(56) References Cited

U.S. PATENT DOCUMENTS

2013/0296823 A1* 11/2013 Melker ............. A61M 5/16854
604/503
2015/0137988 A1* 5/2015 Gravenstein ....... A61B 5/14551
702/19

* cited by examiner

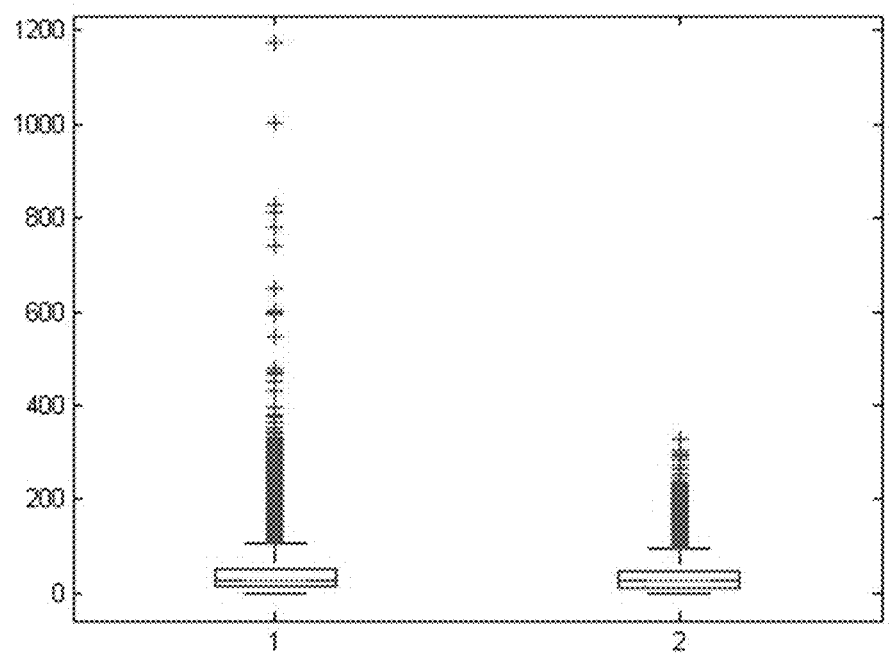
Figure 21: No. 0512 maternity's Peak and Flat data comparison.
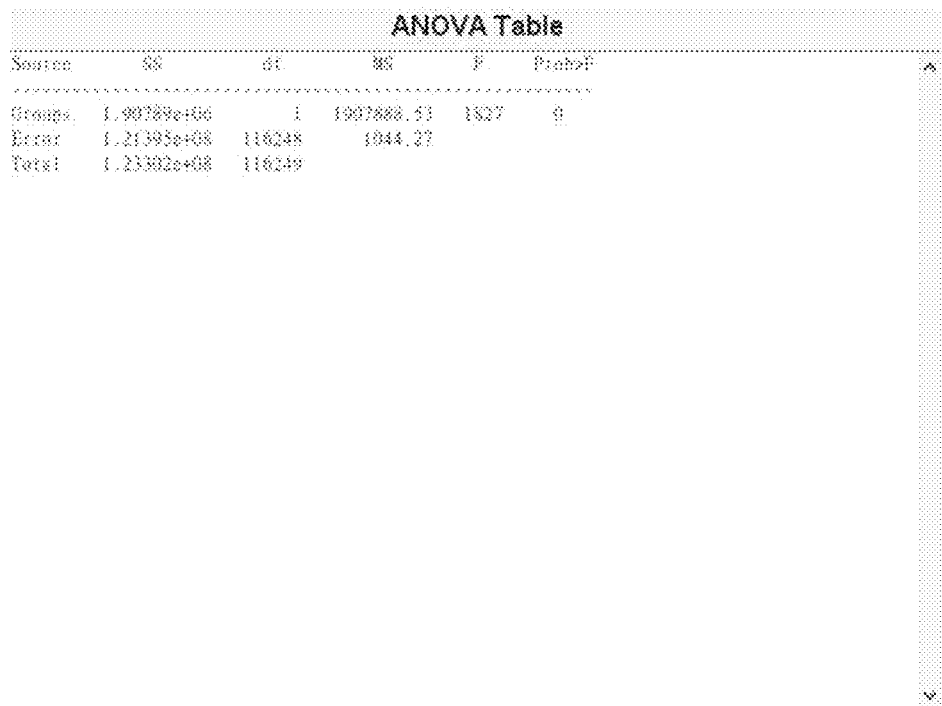
Figure 22: No. 0714 maternity's Anova statistics analysis result, p=0

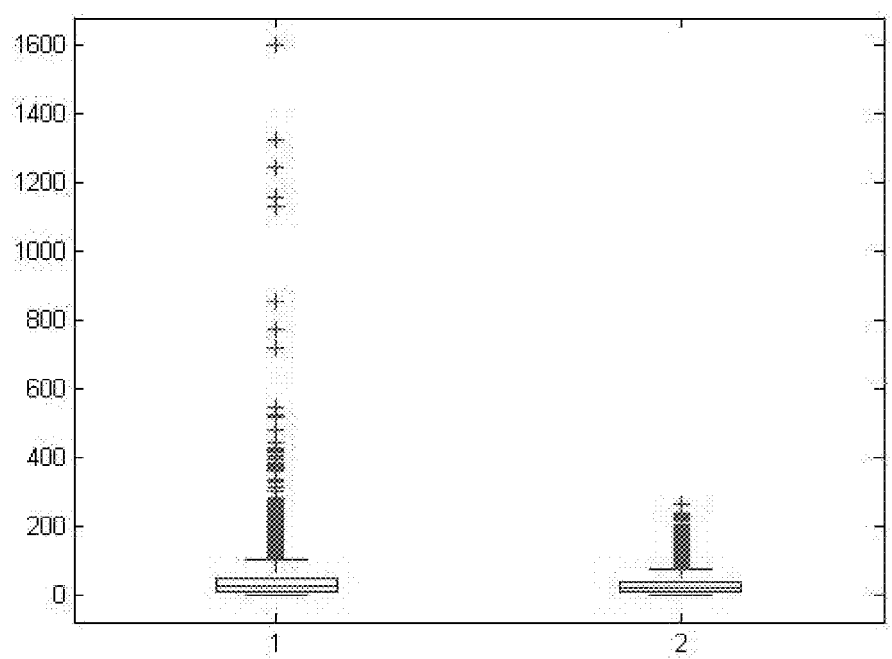
Figure 23: No. 0714 maternity's Peak and Flat data comparison.

REAL-TIME PAIN DETECTION AND PAIN MANAGEMENT SYSTEM

CROSS-REFERENCE TO RELATED APPLICATIONS

This application claims the benefit of U.S. Provisional Application No. 62/772,891, filed on Nov. 29, 2018, and U.S. Provisional Application No. 62/894,532, filed on Aug. 30, 2019, the entire contents of which are hereby incorporated by reference if fully set forth herein.

FIELD OF THE INVENTION

The present invention relates to a system and a method for real-time pain detection by performing an analysis of physiological signals, and a pain management system using said system or method for real-time pain detection.

BACKGROUND OF THE INVENTION

Pain is considered as an unpleasant emotional and sensory experience that may be associated with a real or potential tissue damage. Nowadays, pain is one of the most significant clinical symptoms that can be utilized to detect the acuteness and degree of a patient's injury. However, pain is always subjective where each patient learned the application of the word through experiences related to injury before. Accordingly, it is difficult to objectively measure the levels of pain through a detection of one physiological condition or a method using one parameter relating to one physiological condition.

There are some prior art references disclosing pain monitoring/detection through the measurement of various physiological signals. For example, U.S. Pat. No. 6,117,075 discloses a method and device for determining the depth of anesthesia (DOA) through measurement of skin temperature, or photoplethysmographic pulse pressure to define and analyze the oscillatory pattern, or the correlation between simultaneous oscillatory patterns measured at different physical locations so as to obtain an index of depth of anesthesia.

U.S. Pat. No. 6,685,649 provides a method for monitoring a condition of a patient under an aesthesia or sedation. The method centered and relied upon analysis of a single parameter associated with the cardiovascular system, specifically using time intervals between said successive waveforms, pressures from said successive waveforms, temporal rates from said successive waveforms.

To date, the physiological signals such as skin conductance, blood pressure (BP), heart rate (HR), Electro-Cardio-Gram (ECG), Electro-Encephalo-Graph (EEG), Photo-Plethysmo-Graph (PPG), temperature were reported to be used to determine the depth of anesthesia (DOA) or pain level. However, medical studies have shown that a usage of combination of parameters from different physiological signals significantly improved the pain and no-pain classification performance achieved compared with discrimination using any single signal alone (Guignard, *Clinical anaesthesiology* 20, no. 1: 161-180, 2006).

It was reported to use a group of physiological features to form an Index of Pain or Index of Nociception to determine the state of a patient. For example, U.S. Pat. No. 9,498,138 B2 provides an index called "PMD200," and relates to a system and a method for monitoring by performing a multidimensional analysis of a plurality of physiological signals to generate an index.

It is not considered acceptable for a person to experience untreated severe pain, amenable to safe intervention, while under a physician's care. Pain management should be provided whenever medically indicated. Any pain management technique for patients must be taken into account. Precise prediction of pain intensity could provide valuable insights in situations in which it can be utilized effectively to ultimately determine the position of pain and accordingly to formulate a reasonable therapeutic schedule. Therefore, pain prediction could enhance the quality of daily life for patients in the health-related field of rehabilitation, in-home healthcare and medical emergency services.

U.S. Pat. No. 7,942,818 discloses an obstetric analgesia system for providing a short-acting analgesic agent in the management of pain during labor, where the system enables efficient, real-time prediction of contractions for the coordinated administration of analgesia such that the peak effectiveness of the analgesic coincides with the intermittent pain of labor. However, except the pain during labor is correlated with contractions, there is no way to effectively manage pain via automated analgesic administration because the timing and intensity of pain cannot be predicted.

The heart rate variability based analgesia nociception index (ANI) was reported to reflect different levels of acute pain. The aim of this study was to compare ANI scores with a numeric rating scale (NRS, 0-10) based on self-assessment of pain in the recovery room. disclosed a study of analgesia nociception index (ANI) for evaluation as a new parameter for acute postoperative pain. However, it was concluded that ANI did not reflect different states of acute postoperative pain measured on a numeric rating scale (NRS) after adult sevoflurane-based general anaesthesia (Ledowski et al., *Br. J. Anaesth.* 111(4):627-9, 2013).

Accordingly, it is still desirable to develop a system and a method for detecting or monitoring or identifying the presence and severity of pain that is not reliant on the subjective assessment of pain whenever a patient self-rating of pain cannot be easily obtained (e.g. sedated patients, very young children, individuals with learning difficulties), and furthermore a system and a method for managing pain which is able to determine the timing of administration of an analgesic drug before the initiation of pain.

BRIEF SUMMARY OF THE INVENTION

Accordingly, the present invention provides a system and method for real-time detecting or monitoring pain in a subject, using biomedical signals, such as heart rate, after an analysis and transformation.

In one aspect, the present invention provide a system for real-time detection of pain in a subject, which comprises a means for acquiring biomedical signals relating to pain in a subject in need thereof, a computing means for transforming the acquired biomedical signals during a given period of time into the signal data for measurement of pain, analyzing the data to divide into two or more models, including at least a pain model which is defined by the data showing a peak-shaped profile and a non-pain model which is defined by the data showing a flat profile, whereby the pain status of the subject is measured based on the results of the analysis, a process means for generating an index of pain using the results of the analysis depending on the subject's demands or sensation, and a display showing the pain status of the subject.

In another aspect, the present invention provides a method for real-time monitoring pain in a subject, comprising acquiring biomedical signals relating to pain in said subject, transforming the acquired biomedical signals during a given period of time into the signal data for measurement of pain, analyzing the data to divide into two or more models, including at least a pain model which is defined by the data showing a peak-shaped profile and a non-pain model which is defined by the data showing a flat profile, whereby the pain status of the subject is measured based on the results of the analysis, a process means for generating an index of pain using the results of the analysis depending on the subject's desire or sensation.

In one embodiment of the invention, the biomedical signals are signals relating to heart rates, including but not limited to heart rate (HR), pulse rate (PR), heart rate variability (HRV), and electrocardiogram (ECG).

In one preferred embodiment of the invention, the biomedical signals are electrocardiogram (ECG).

According to the invention, the data are analyzed to obtain a pain index g(k), which is defined by the formula below $$g(k) = \frac{(|FFT'(k)| - |FFT'_{Flat}(i)|)}{a * std(FFT'_{Flat}(i))} * 100\%$$

in which FFT'(k) indicates a continuous ECG Data and its period samples are S_pt; and a is set by the subject's pain sensation.

In a further aspect, the present invention provide a system for management of pain in a subject, comprising a system for real-time detection of pain according to the invention, and an analgesia system for delivering an analgesic agent or performing a pain relief method, and a means for communication between the system for real-time detection of pain and the analgesia system; wherein the analgesia system is initiated before pain, and the administration of the analgesic agent or the pain relief method performs based on the timing or intensity of pain as detected by the system for real-time detection of pain.

In one embodiment of the invention, the analgesia system is provided for the administration of short acting intravenous, transdermal, transmucosal, or intramuscular analgesia, that supplies improved pain relief.

In one embodiment of the invention, the analgesic agent is a drug or an agent that is highly titratable, with a rapid and predictable onset, and a short duration of bioactivity.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1:
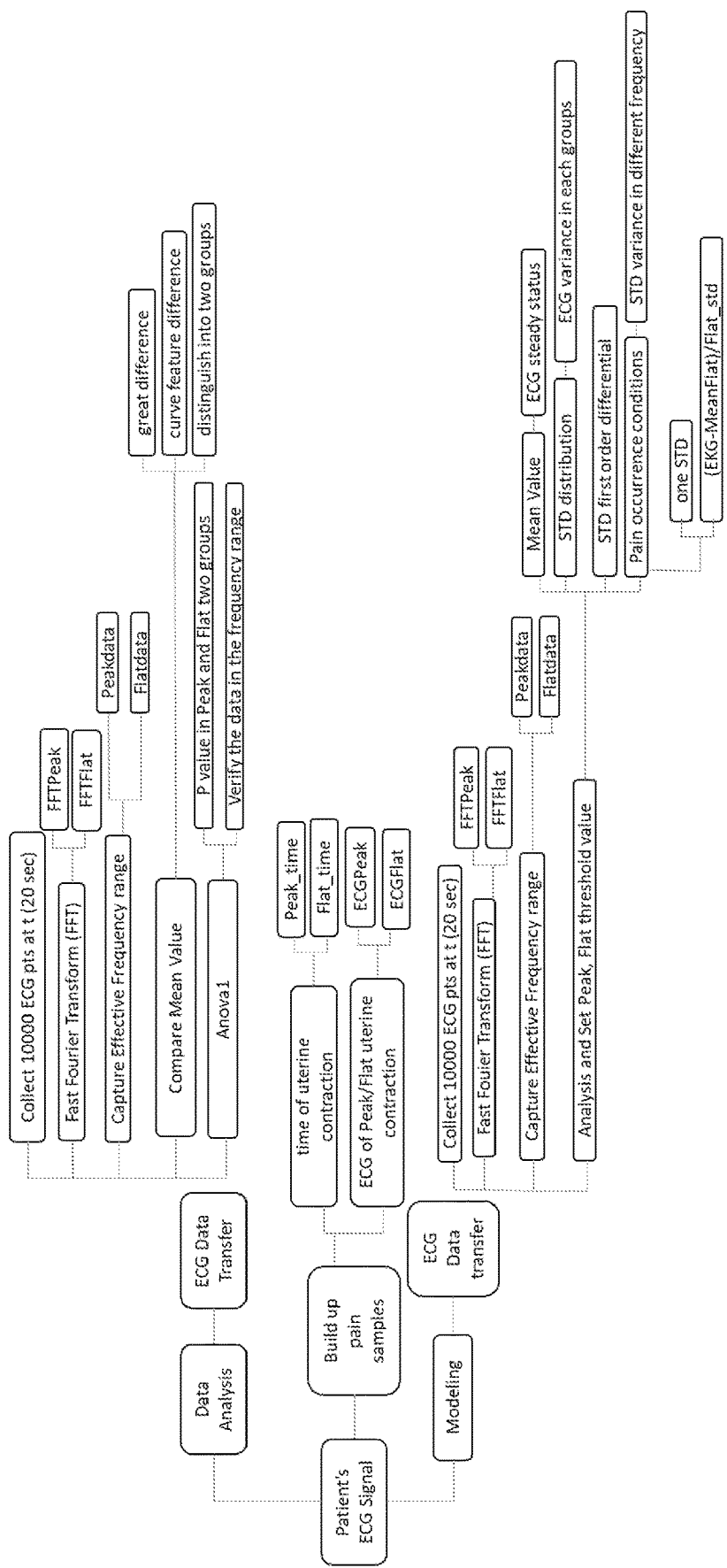

FIG. 1 provides an analysis architecture diagram according to the invention.

Figure 2:
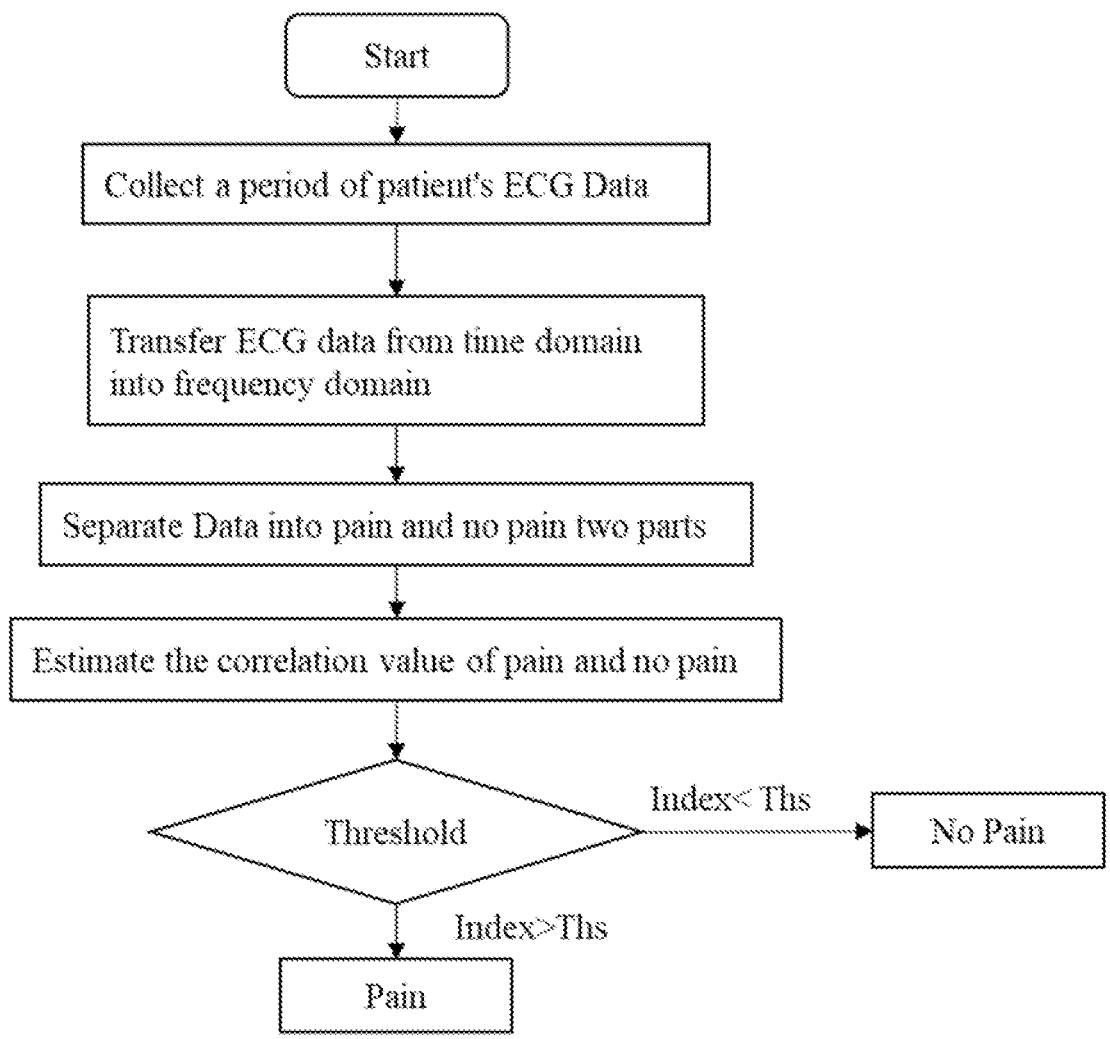
Figure 3:
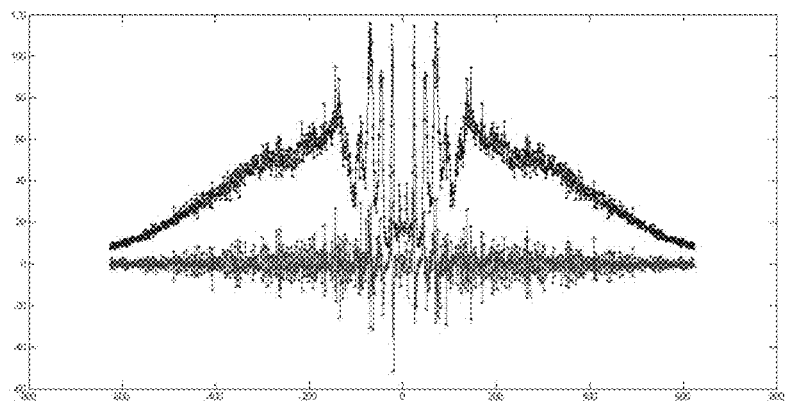

FIG. 2 provides the flow char for the pain monitoring system according to the invention FIG. 3 provides a pain module, wherein the signals in blue are the $FFT_{Flat}(i)$ standard deviation distribution, the signals in red are the first order of $FFT_{Flat}(i)$ standard deviation distribution.

Figure 4:
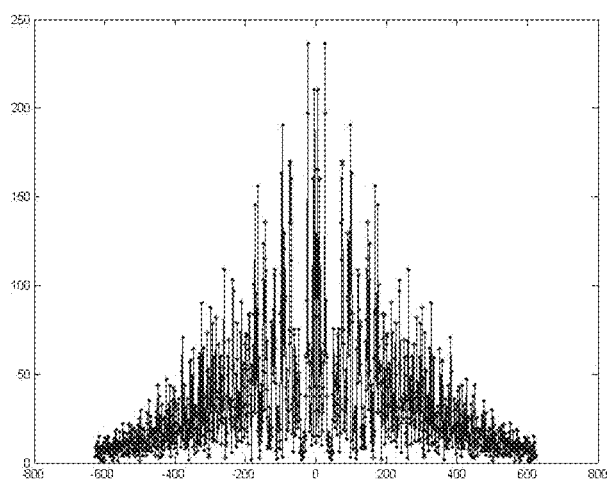

FIG. 4 shows the fast fourier transform of ECG and labeled as $FFT_{Flat}(i)$ in one embodiment of the invention.

Figure 5:
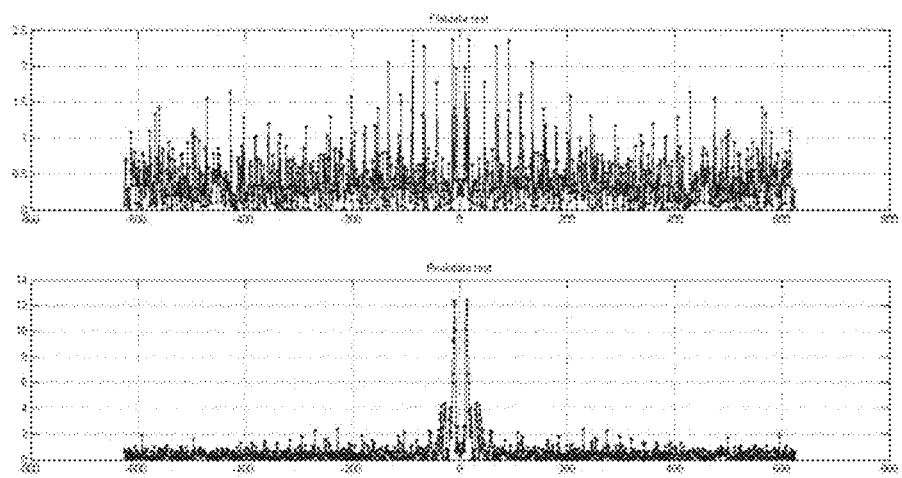

FIG. 5 shows the result of ECG Peak and Flat test data; wherein the upper graph is ECG at Flat uterine contraction test data; and the lower graph is ECG at Peak uterine contraction test data.

Figure 6:
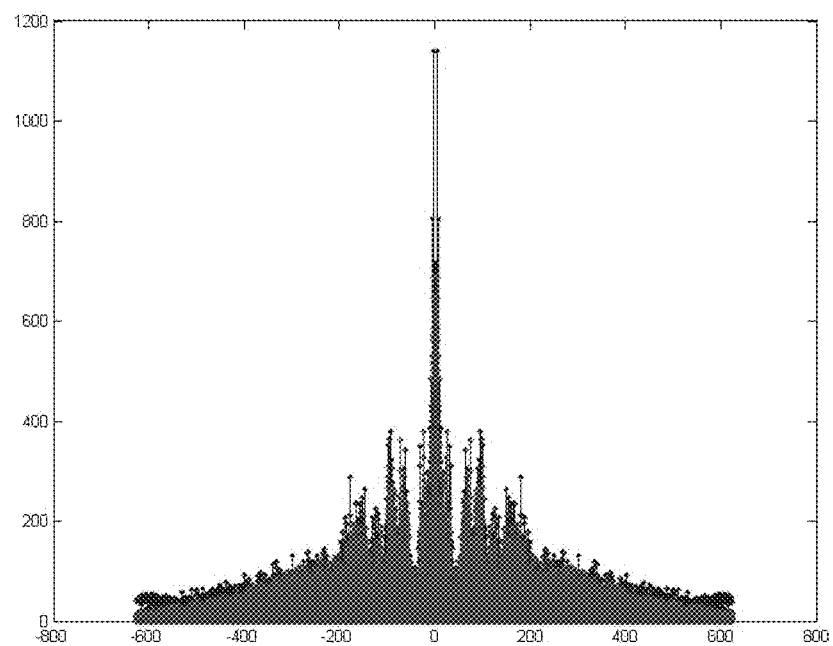

FIG. 6 shows the Peak and Flat original FFT accumulation result; wherein the signals in red are Flat FFT data and the signals in blue are Peak FFT data in Case 1.

Figure 7:
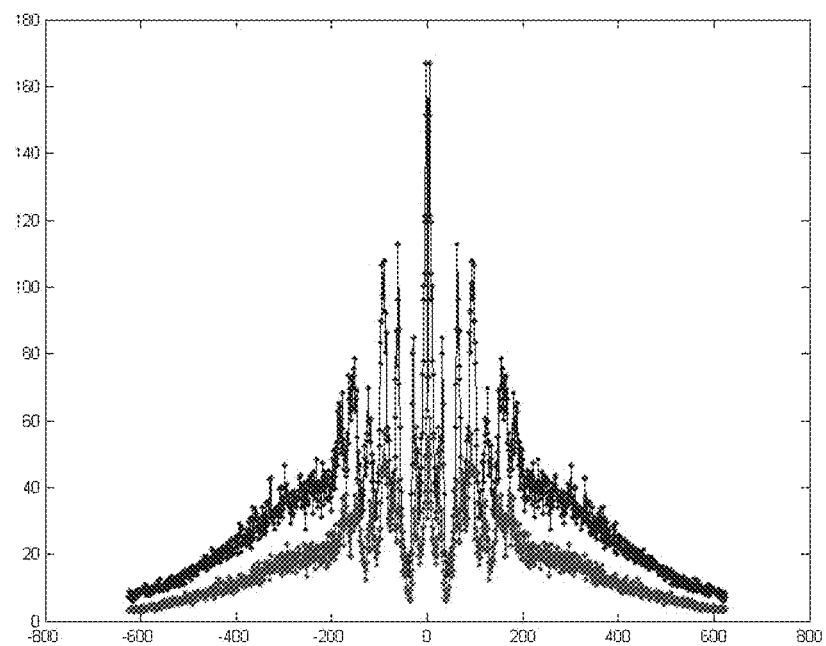

FIG. 7 shows the Peak and Flat FFT original mean value distribution in Case 1.

Figure 8:
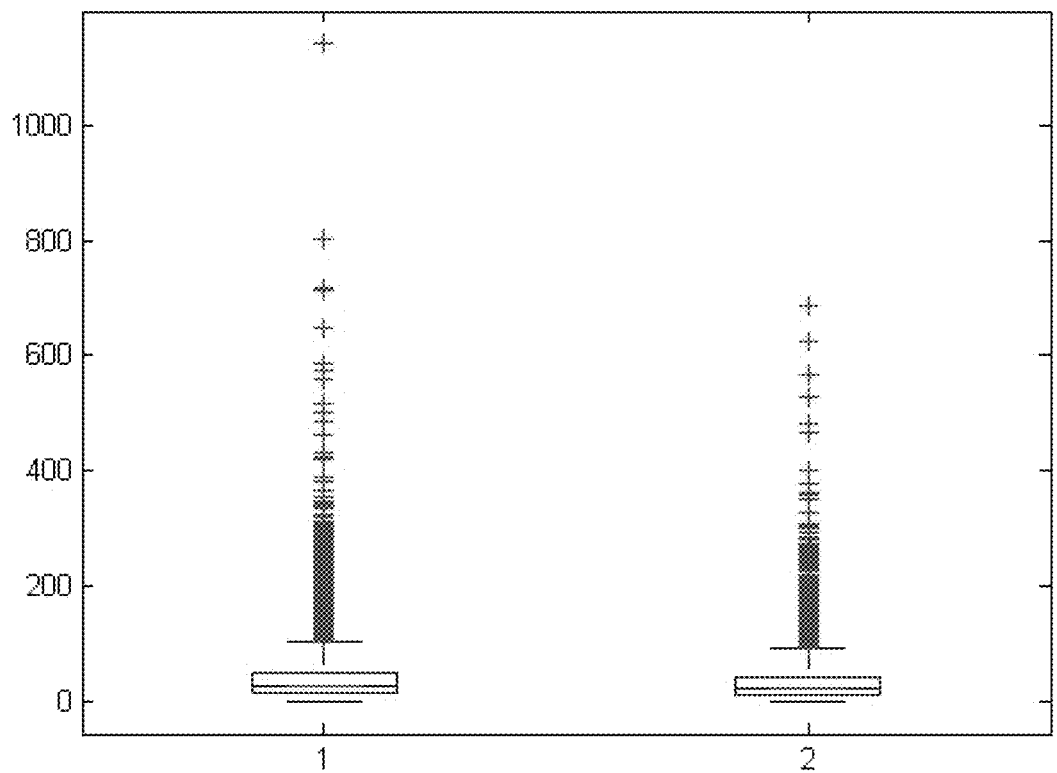

FIG. 8 shows the comparison between the Peak and Flat data in Case 1.

Figure 9:
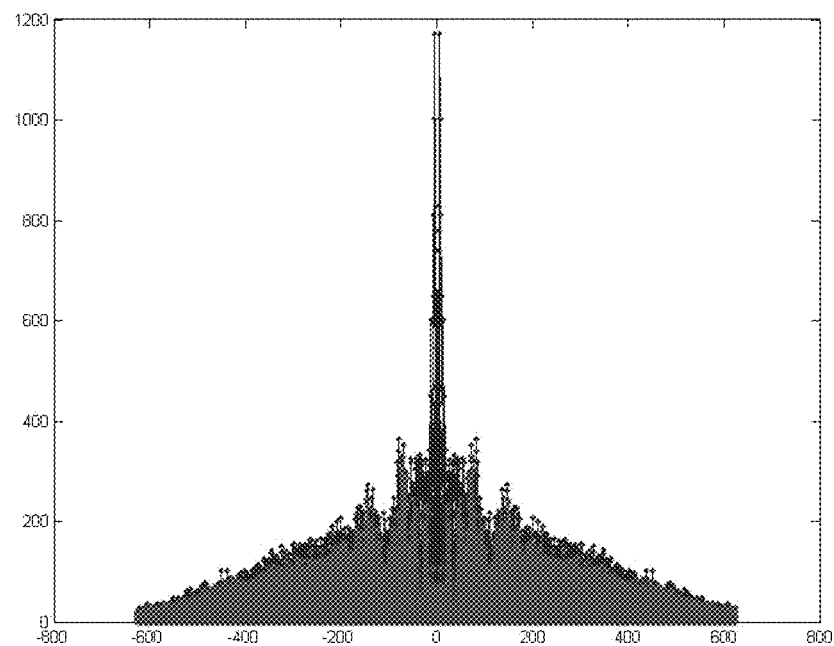

FIG. 9 shows the Peak and Flat original FFT accumulation result; wherein the signals in red are Flat FFT data and the signals in blue are Peak FFT data in Case 2.

Figure 10:
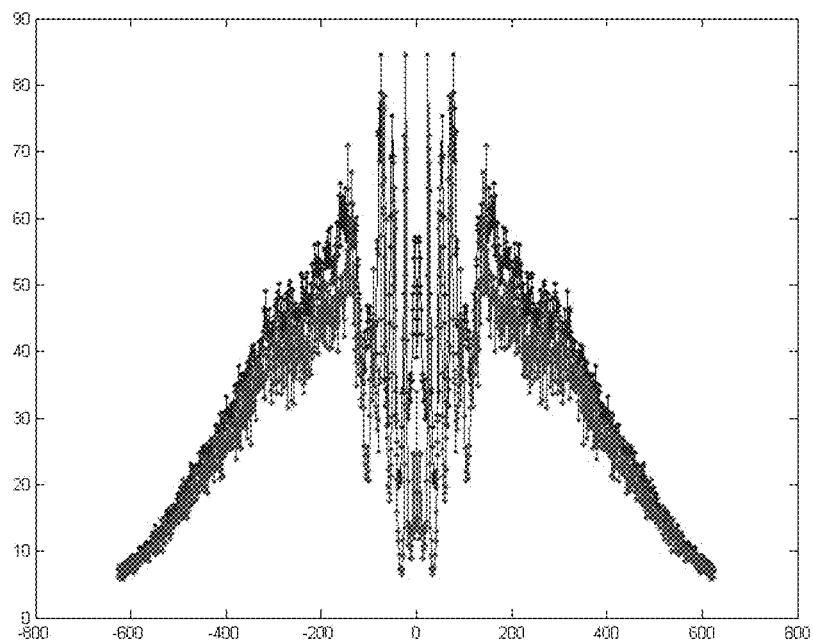

FIG. 10 shows the Peak and Flat FFT original mean value distribution in Case 2.

Figure 11:
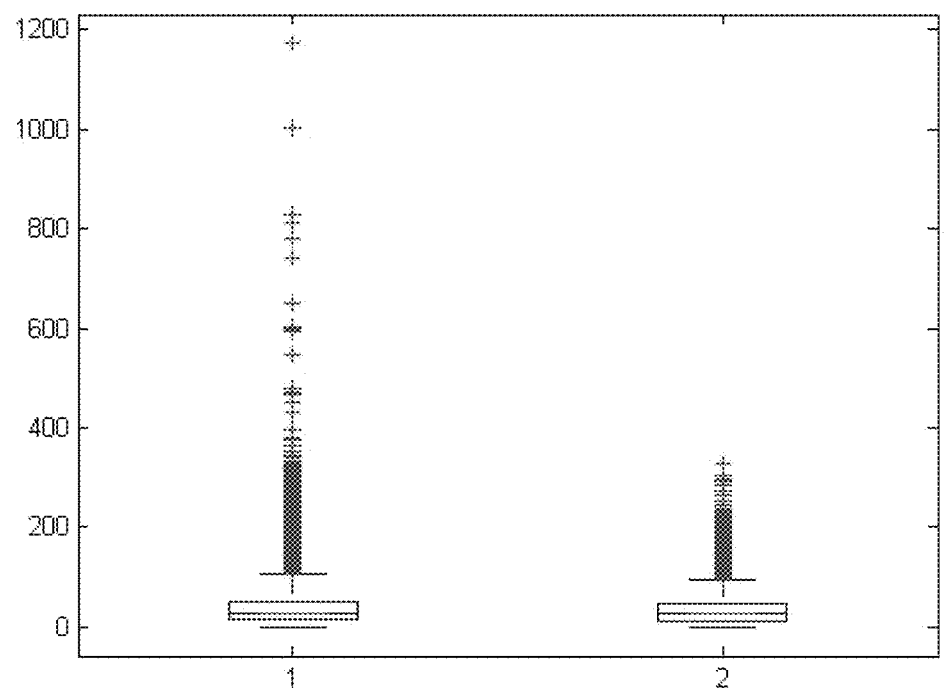

FIG. 11 shows the comparison between the Peak and Flat data in Case 2.

Figure 12:
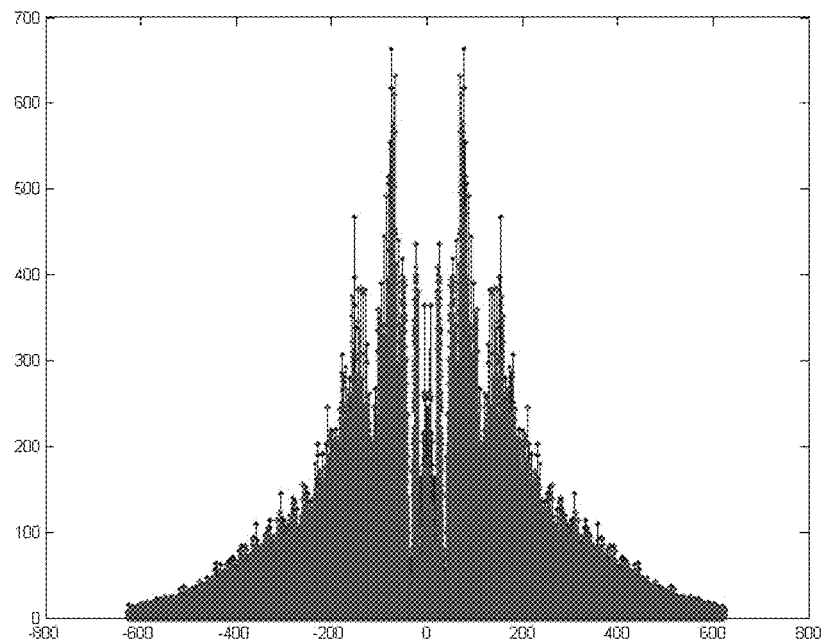

FIG. 12 shows the Peak and Flat original FFT accumulation result; wherein the signals in red are Flat FFT data and the signals in blue are Peak FFT data in Case 3.

Figure 13:
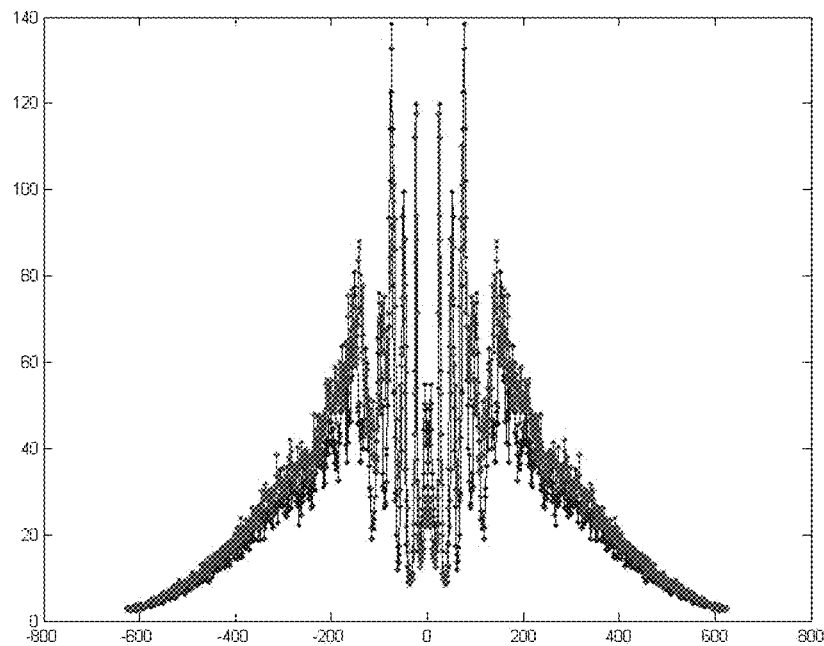

FIG. 13 shows the Peak and Flat FFT original mean value distribution in Case 3.

Figure 14:
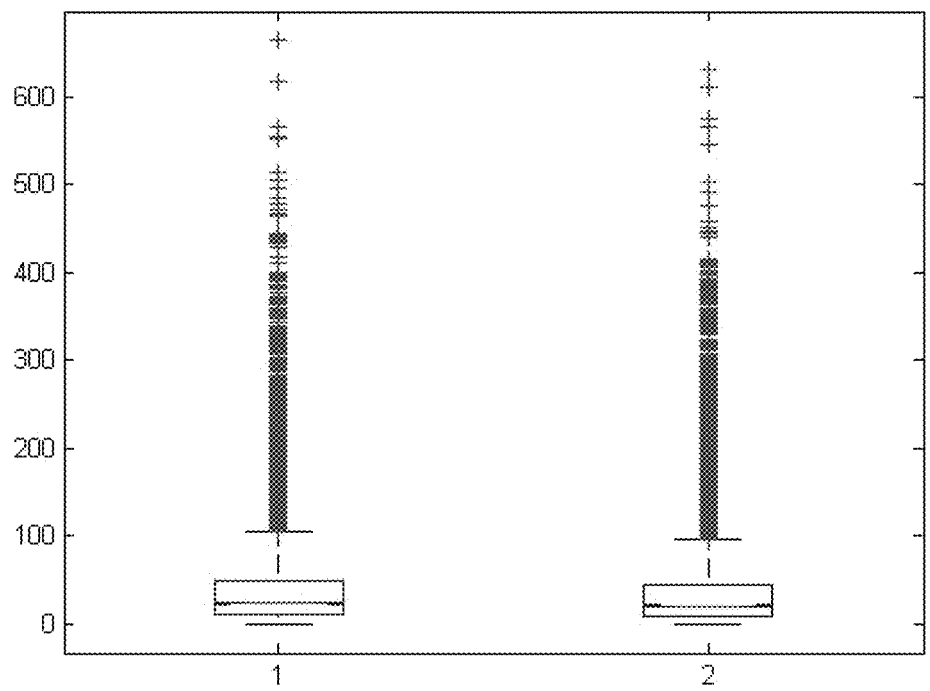

FIG. 14 shows the comparison between the Peak and Flat data in Case 3.

Figure 15:
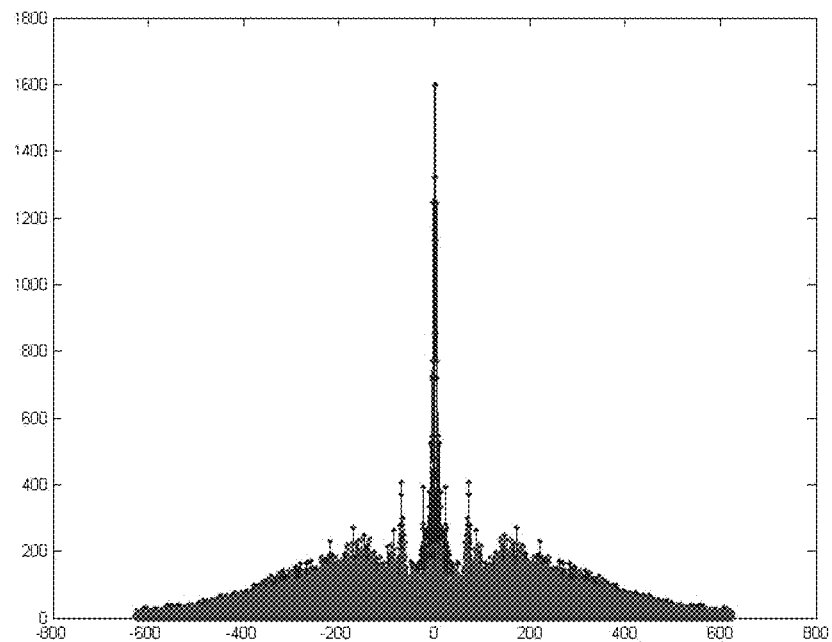

FIG. 15 shows the Peak and Flat original FFT accumulation result; wherein the signals in red are Flat FFT data and the signals in blue are Peak FFT data in Case 4.

Figure 16:
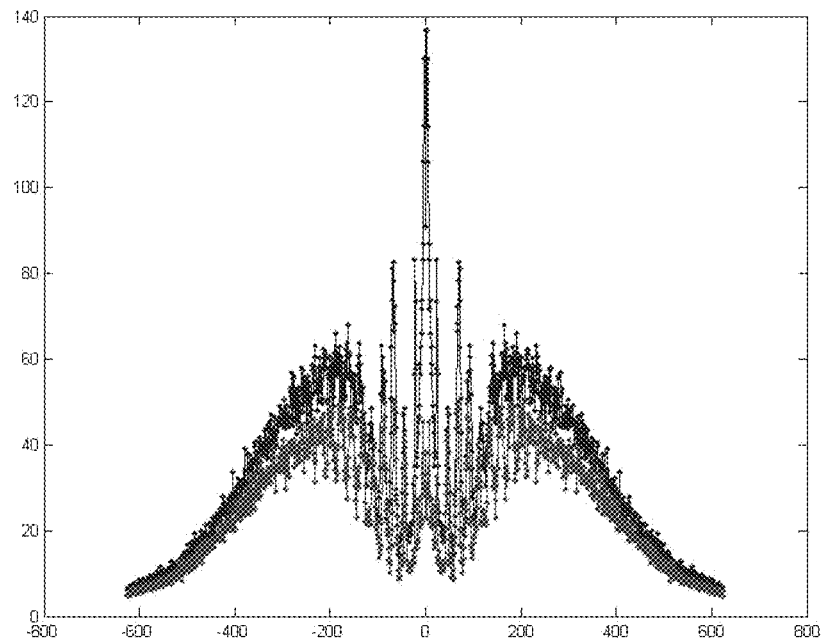

FIG. 16 shows the Peak and Flat FFT original mean value distribution in Case 4.

Figure 17:
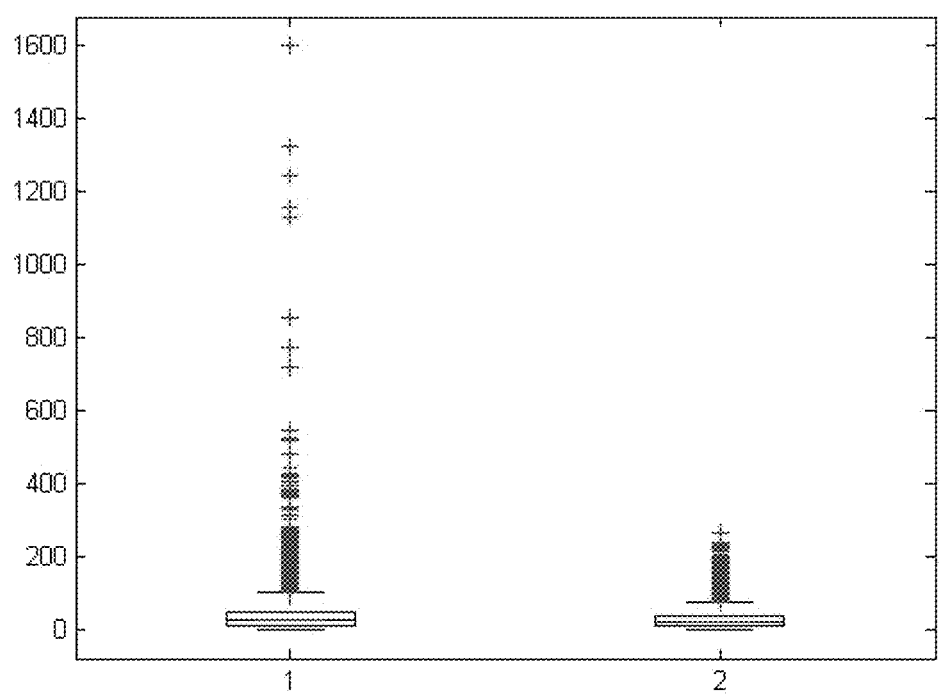

FIG. 17 shows the comparison between the Peak and Flat data in Case 4.

Figure 18:
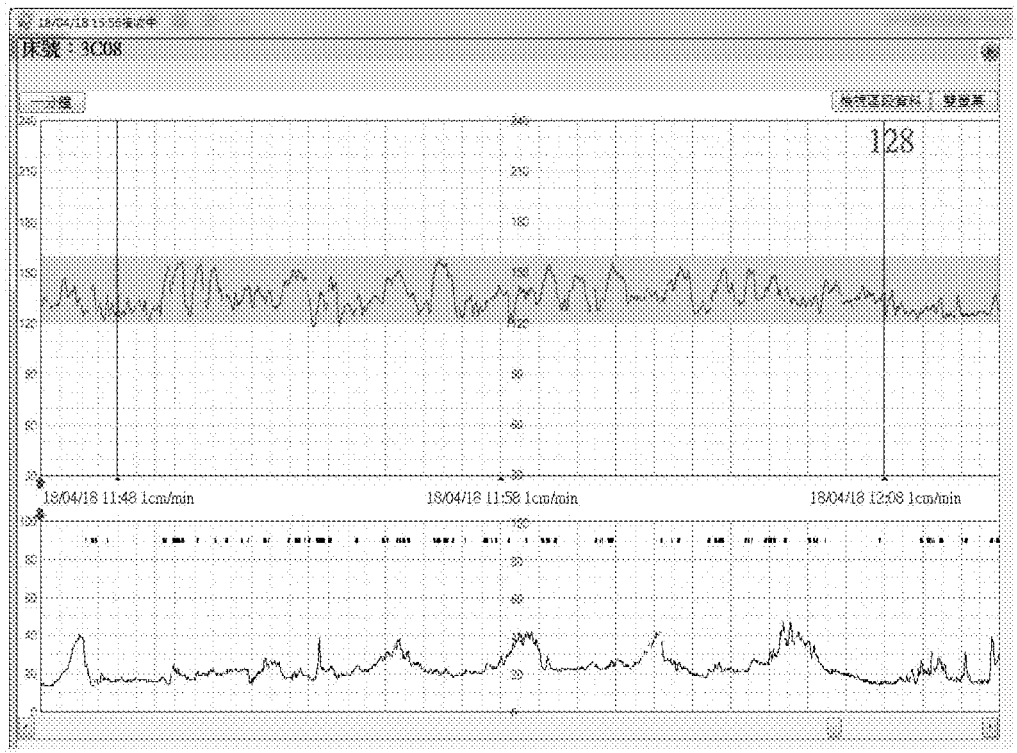

FIG. 18 shows the uterine contraction of Maternity.

Figure 19:
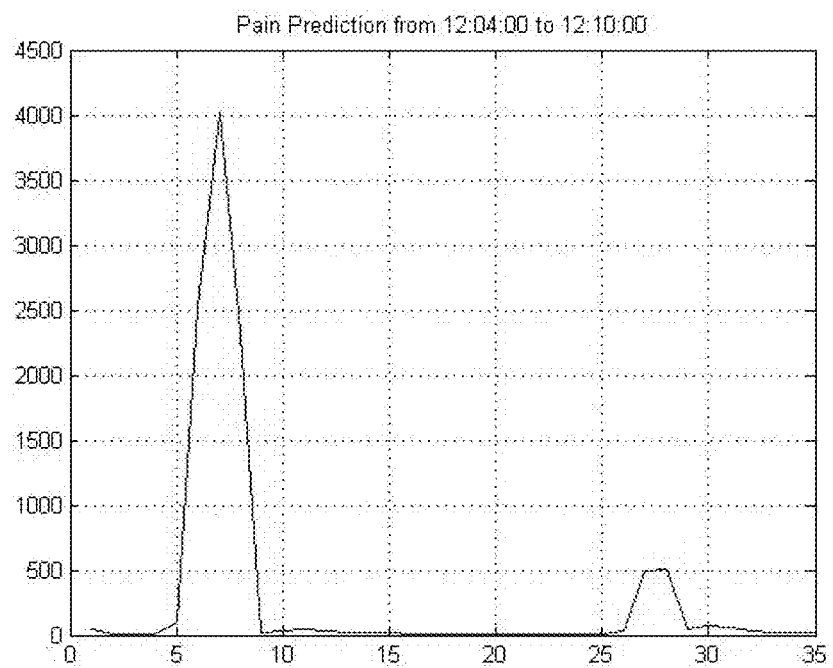

FIG. 19 shows the analysis results; wherein the point pt_4 is the time "12:04:30" and the end of point pt_13 is the time; wherein a period ECG data is given and the pain of Maternity is predicted from 12:04:00~12:10:00, cycle=10 sec; $g_{ratio}$=1.5, Alpha=1.

Figure 20:
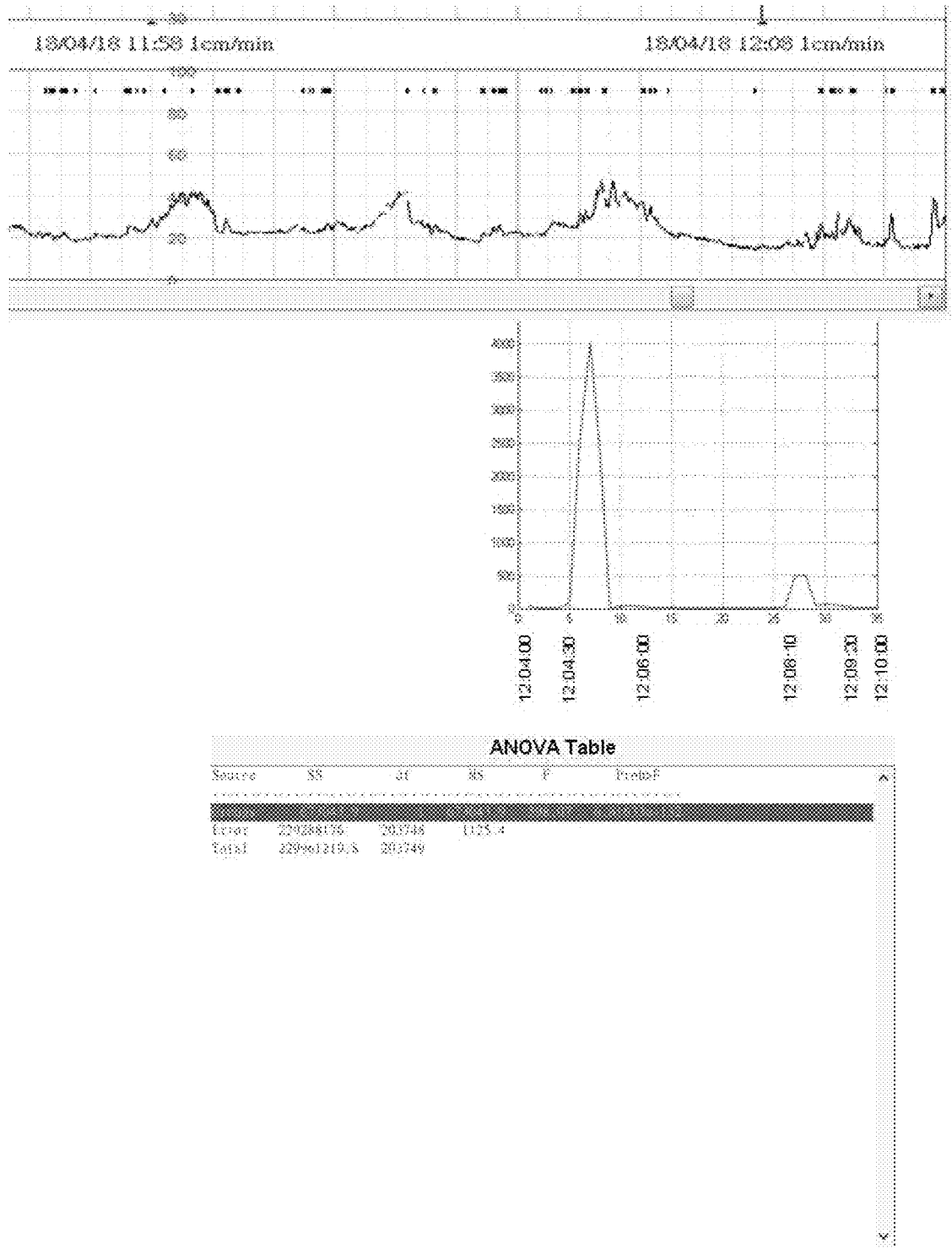

FIG. 20 shows the No. 0512 maternity's Anova statistics analysis result, p=6.81633×10$^{-132}$, wherein the point pt_12 is the time "12:06:00," the point pt_26 is the time "12:08:10" and the end of point pt_33 is the time "12:09:20."

FIG. 21 show the No. 0512 maternity's Peak and Flat data comparison.

FIG. 22 shows the No. 0714 maternity's Anova statistics analysis result, p=0.

FIG. 23 shows the No. 0714 maternity's Peak and Flat data comparison.

DETAILED DESCRIPTION OF THE INVENTION

Unless defined otherwise, all technical and scientific terms used herein have the same meaning as commonly understood by a person skilled in the art to which this invention belongs.

The invention provides a system for real-time detection of pain in a subject, which comprises a means for acquiring biomedical signals relating to pain in a subject in need thereof, a computing means for transforming the acquired biomedical signals during a given period of time into the signal data for measurement of pain, analyzing the data to divide into two or more models, including at least a pain model which is defined by the data showing a peak-shaped profile and a non-pain model which is defined by the data showing a flat profile, whereby the pain status of the subject is measured based on the results of the analysis, a process means for generating an index of pain using the results of the analysis depending on the subject's demands or sensation, and a display showing the pain status of the subject.

On the other hand, the present invention provides a method for real-time monitoring pain in a subject, comprising acquiring biomedical signals relating to pain in said subject, transforming the acquired biomedical signals during a given period of time into the signal data for measurement of pain, analyzing the data to divide into two or more models, including at least a pain model which is defined by the data showing a peak-shaped profile and a non-pain model which is defined by the data showing a flat profile, whereby the pain status of the subject is measured based on the results of the analysis, a process means for generating an index of pain using the results of the analysis depending on the subject's desire or sensation.

In addition, the invention provides a system for management of pain in a subject, comprising a system for real-time detection of pain according to the invention, and an analgesia system for delivering an analgesic agent or performing a pain relief method, and a means for communication between the system for real-time detection of pain and the analgesia system; wherein the analgesia system is initiated before pain, and the administration of the analgesic agent or the pain relief method performs based on the timing or intensity of pain as detected by the system for real-time detection of pain In the invention, the biomedical signals as used may be any physiological signals relating to heart rates. Currently available technologies that can analyze and monitor physiological signals relating to heart rates include, but are not limited to, heart rate (HR), pulse, heart rate variability (HRV), blood volume pulse (BVP), or electrocardiogram (ECG). These signals reflect the activity level of the autonomic nervous system, which is connected with the secretory activity of cardiac muscles and internal organs.

The term "heart rate" or "HR" or "pulse" used herein refers to the speed of the heartbeat measured by the contractions (beats) of the heart per minute (bpm).

The term "heart rate variability" or "HRV" as used herein refers to the physiological phenomenon of variation in the time interval between heartbeats, which may be measured by the variation in the beat-to-beat interval.

The blood volume pulse (BVP) signals are derived from a photoplethysmographic (PPG) sensor that monitors blood volume in capillaries and arteries by emitting an infrared light through the tissues. Hence, changes in BVP amplitude reflect instantaneous sympathetic activation. Most PPG sensors can be placed anywhere on the body, with the finger as the most common location for recording a BVP signal.

The electrocardiogram (ECG), which is an electro physiological signal associated with the electrical activity of the sinuatrial node, reflects the cardiovascular activity. Additionally, ECG responses to external stimuli (such as pain stimuli and stress) can produce large variability in a given subject's physiological signal. Therefore, we can employ ECG signal to extract universal information about pain state or intensity.

In one example of the present invention, ECG data, when detected reliably at its onset, can be used as an effective precursor for defining the pain and non-pain model for use in the coordinated delivery of an analgesic agent so that the analgesic's pain-relieving ability coincides with a pain cycle.

In an embodiment of the invention, the pain management system further comprises a means for delivering a short-acting analgesic to the subject in advance of the pain so that the pain-relieving ability of the analgesia peaks with the pain. For example, the pain management system comprises a means for providing an audible or visible warning signal to notify.

In the invention, the subject pain management system further provides a means for triggering the delivery of an analgesic.

In another embodiment of the invention, the pain management system is provided that has an automated analgesic delivery feature for automatic delivery of an analgesic agent, and/or adaptive alteration of the analgesic concentration based on monitored the biomedical signals relating to heart rates (e.g., via monitored ECG).

In a related embodiment of the invention, the pain management system can determine the extent of pain, and based on the data, alter the analgesic concentration. This "extent of pain," referring to the time and/or intensity of a pain, may be determined from either (1) the current ECG; (2) the time history of the ECG; or (3) via patient input into the system, and/or through some combination of (1)-(3) above, depending on the pain extent of the subject, varied on the subject's demands or sensations.

In the example of the invention, the ECG signals from time domain to frequency domain was transformed and then the data is divided into two kinds of profiles, and analyzed to figure out the feature and difference between the "pain" and "non-pain" models.

In the invention, the pain management system is provided that automatically delivers an analgesic agent in advance of pain. The system preferably accepts a patient input to titrate the dose of the analgesic agent. In a related embodiment, the pain management system preferably controls the delivery of an analgesic agent, while continuously monitoring patient clinical status with pulse oximetry. In another related embodiment, the analgesia system preferably controls a transdermal, transmucosal or intramuscular administration system.

In operation, a monitoring means is used to collect biomedical data relating to pain, which is clinically relevant data regarding pain. The computing means is provided to analyze the collected biomedical signals, and then transmit the biomedical data to establish pain models. The pain model can be defined by algorithms for determining data such as onset of pain, pain frequency, pain duration, pain intensity, time history of pain cycles, and the like. Based on the determined time for analgesic delivery, the analgesic delivery means is activated to deliver the analgesic to the patient.

In the present invention, an analysis architecture diagram is given in FIG. 1.

Exaction of Clinical Biomedical Data

There are various technologies currently available to the clinician for extracting biomedical data relating to pain that can be used in accordance with the present invention to establish pain model (including for example, onset of pain, pain frequency, pain duration, and the like).

In one embodiment, detection of biomedical data relating to pain for use with the analgesic system of the invention can be performed using a conventional method or measurement. In the invention, any available technologies that can analyze and monitor physiological signals relating to pain include, but are not limited to, blood volume pulse (BVP), electrocardiogram (ECG), and skin conductance level (SCL). These signals reflect the activity level of the autonomic nervous system, which is connected with the secretory activity of cardiac muscles and internal organs.

In the present invention, the biomedical data relating to pain may be any clinical data, including the data for the determination of the absence, presence, and intensity of pain (Cruccu et al., 2010; Haanpääet al., 2011), such as Numeric Pain Rating Scales (NPRS), Verbal Rating Scales (VRS), and Visual Analog Scales (VAS) (Frampton and Hughes-Webb, 2011). These self-reported scales are especially well applied and validated in cancer patients (Caraceni et al., 2002). In addition, the McGill Pain Questionnaire (MPQ) and Brief Pain Inventory are also used to assess the wider pain perception in multidimensional scales (Frampton and Hughes-Webb, 2011). While self-descripted pain provides important clinical reference indicators and proves to be a valid method for the adequate therapy of patients suffered from pain in most situations (Brown et al., 2011). In addition, the pain assessment on recognition and prediction from human behaviors may also be used, including vocalizations (Puntillo et al., 2004), body motions (Young et al., 2006), and facial expressions (Lucey et al., 2011; Kaltwang et al., 2012; Irani et al., 2015). While behavioral methods exist, they also may be inapplicablle in individuals with paralysis or other motor disorders affecting behaviors. By observing the face of an individual, a huge number of features related with affective state can be extracted, including pain state. The measurement focused on diverse bio-physiological signals, such as heart rate variability (De Jonckheere et al., 2010, 2012; Faye et al., 2010; Logier et al., 2010), skin conductance or electrodermal activity (Harrison et al., 2006; Treister et al., 2012), electromyography (Oliveira et al., 2012), electroencephalography (Nir et al., 2010; Huang et al., 2013), and functional magnetic resonance imaging (fMRI) (Marquand et al., 2010; Brown et al., 2011) may also be used. Pain assessment method implemented by multimodality signals has been confirmed to be highly effective, some even outperforming single-signal mode markedly (Werner et al., 2014; Kächele et al., 2015). The quantitative measurement of pain intensity from multi-physiological signals obtained by wearable sensors. The automatic recognition of pain intensity from physiological signals may also be included, such as electromyography (EMG) and body motions in combination with Support Vector Machines (SVM) and Random Forests (RF) as classifiers to recognize three pain intensity (Olugbade et al., 2015). Kachele et al. used EMG, skin conductance level (SCL) and electrocardiogram (ECG) incorporated with unsupervised and semi-supervised learning to establish a personalized system of continuous pain intensity recognition (Kachele et al., 2016).

Establishment of Pain Models

The system of the subject invention comprises a computing means for analyzing the collected biomedical signals to define the pain and non-pain model (such as ECG data). In a preferred embodiment, the computing means to define pain and non-pain models, which contains means for receiving and -analyzing sensor input to accurately determine the onset of pain, pain frequency, pain duration, pain intensity, time of history of pain cycles, and the like. A graphical user interface can be included with the systems of the invention to display biomedical data relating to pain, pain models, as well as enable user-interaction.

In one embodiment, the system of the invention further includes an intelligence system that can use the biomedical data relating to pain generated by the computing means in offering biomedical clinical data for determining the onset of a pain cycle. In addition, the intelligence system can be provided in the analgesic system of the invention to enable real-time assistance in providing a support in the management of pain (i.e., type of analgesic to administer, likelihood of delivery within a period of time, etc.).

In accordance with the subject invention, the computing means is preferably a digital signal processor, which can (1) automatically, accurately, and in real-time, extract biomedical signals such as ECG signals, from sensor input; (2) assess the quality of biomedical data provided by the processor in view of environmental noise; and (3) determine, based on the biomedical data, onset of pain, pain frequency, pain duration, pain intensity, and the like.

Biomedical signals (i.e., ECG signals, etc.) collected in accordance with the present invention are transmitted from the data extraction to the computing means for signal processing. The computing means can also be responsible for maintenance of the collected biomedical data as well as the maintenance of the analgesic system itself. The computing means can also detect and act upon user input via user interface means known to the skilled artisan.

In certain embodiments, the computing means comprises a memory capacity sufficiently large to perform algorithm operations in accordance with the present invention. The memory capacity of the invention can support loading a computer program code via a computer-readable storage media, wherein the program contains the source code to perform the operational algorithms of the subject invention. Optionally, the memory capacity can support directly programming the CPU to perform the operational algorithms of the subject invention. A standard bus configuration can transmit data between the CPU, memory, ports and any communication devices.

Communication devices such as wireless interfaces, cable modems, satellite links, microwave relays, and traditional telephonic modems can transfer biomedical data from a computing means to a provider via a network. Networks available for transmission of the biomedical data include, but are not limited to, local area networks, intranets and the open internet.

According to the subject invention, novel obstetric analgesic systems are provided that include a patient controlled analgesia (PCA) feature that enables the patient to auto-mated-administer pain medicine after a signal is communicated regarding the onset of pain.

In a common form of PCA for use in the subject invention, the subject is provided with a mechanical apparatus comprised of a reservoir and a patient-operable pump. On patient demand, the pump dispenses incremental doses of pain medicine from the reservoir into the subject's intravenous (IV) system. The device may also comprise a lock-out interval feature that prevents patient remediation for a period of time so as to ensure against over-medication.

The system for pain management according to the invention comprises an analgesia system, which includes, but is not limited to: intravenous, subcutaneous, intramuscular, intra-articular, parenteral, peritoneal, intranasal, iihalational, oral, rectal, intravaginal, topical, nasal, ophthalmic, topical, transcutaneous, sublingual, epidural, intrathecal, delivery of pain medications (such as analgesics, anesthetics, sedatives, tranquilizers, or narcotic antagonist combinations) or electrical stimulation of the spinal nerves (such as with transcutaneous electrical nerve stimulation (TENS)).

Pain medications that can be automatically delivered based on established contraction data in accordance with the present invention. In certain embodiments, pain medications that cause loss of sensation are automatically delivered via any one of the following methods: local block, paracervical block, pudendal block, epidural anesthesia and analgesia, spinal anesthesia and analgesia, and inhalational anesthesia.

The present invention is illustrated in the following embodiments and examples.

The definitions of symbols are given below:
TPeak(i): the timing of Peak in Uterine contraction graph;
TFlat(j): the timing of Flat in Uterine contraction graph;
S_pt: 10000 sampling points, total duration is 20 sec;
ECG(n): maternity's ECG record;
F: Frequency=1000 ms/512 sampling points;
Fcut: Cut Frequency.

1. Pain Model Implementation
1.1 Data Extraction

Each maternity's uterine contractions was compared with her ECG patterns in the labor duration. The timing of peak in uterine contraction graph is labeled as TPeak(i). The timing of flat in uterine contraction graph is labeled as TFlat(i). When maternity's uterine contraction is on the peak or flat timing T(i), we capture the 10000 ECG signals during the T(i). ECG sampling frequency is 512 Hz, total 10000 pts is 20 sec. We label the ECG at the peak of uterine contraction as $ECG_{Peak}(i)$, and the flat of uterine contraction as $ECG_{Flat}(i)$.

1.2 Data Processing

First, We collect 10000 ECG(i) signal points. Second, we do the Fast Fourier Transform (FFT), and obtain the results $FFT_{peak}(i)$, $FFT_{Flat}(i)$. Third, setting the Cut Frequency $F_{cut}$ to focus the greater difference between peak and flat FFT results, and compare their pain statistics data. Finally, we divide ECG Data into Peak and Flat two groups, and calculate each mean value and standard deviation.

In the four maternities' examples, the mean value of each Peak and Flat shows obvious difference. ANOVA was used to test Peak and Flat two groups, and obtain a strong significant difference.

1.3 Model Implement

Based on the hypothesis that the highest Peak point of the uterine contraction map is the time point of pain, and the lowest Flat point of the uterine contraction map is the time of non-pain. According the result of $FFT_{Peak}(i)$ defining the pain model and $FFT_{Flat}(i)$ defining the non-pain model, these two kinds of FFT groups signal have obviously great difference. It means that an effective frequency domain analysis graph can be obtained by FFT conversion in 20 sec ECG signal. We can compare the FFT(i) data with Flat general graph and judge the occurrence of pain.

We calculated the mean value and standard deviation of $FFT_{Peak}(i)$ and $FFT_{Flat}(i)$. From the mean value distribution, we took one standard deviation to be the effective pain model observation range. For enhancing difference, accelerating calculating and decreasing judging time, we computed first order differential of Peak (defining as a pain model) and Flat (defining as a no-pain model) standard distribution. The variance of each frequency was shown and a threshold of the pain occurrence timing could be set in the experience data.

ECG signals were randomly collected from a patient and its FFT(i1) distribution was computed, and then the difference of mean value between FFT(i1) and $FFT_{Flat}(i)$ was calculated. Then, the ratio of the difference value to $FFT_{Flat}(i)$ standard deviation was calculated. If the difference in low frequency over 200% or accumulation of full frequency over 100% is to great, this ECG(i) was determined in the duration of pain. The result of the pain module analysis was shown in FIG. 2.

2. Operation Functions
2.1 Extract Peak uterine contraction
a. Extract ECG(n) at TPeak(i) and labeled as n (TPeak(i))
b. Acquire the pain data showing a peak profile:

$$ECG_{Peak}(i) = ECG\left[(n(T_{Peak}(i)) - \frac{S\_pt}{2} \ldots (n(T_{Peak}(i)) + \frac{S\_pt}{2}\right]$$

c. Compute $ECG_{Peak}(i)$ frequency domain data via Fast Fourier Transform (FFT), and defined as $FFT_{Peak}(i)$. From $FFT_{Peak}(i)$ distribution, we can figure out the difference of the pain between pain or no pain.
d. Keep the effective data from −F_cut to F_cut, a constant value of samples points.

$$FFT_{Peak}(i) = \begin{cases} FFT_{Peak}(i); & -F_{Cut} < f < F_{cut} \\ 0; & \text{otherwise} \end{cases}$$

The Fast Fourier Transform of ECG and labeled as $FFT_{Peak}(i)$ was shown in FIG. 3. 2.2 Extract Flat uterine contraction
a. Extract ECG(n) at TFlat(i) and label as n (TFlat(i))
b. Acquire the pain data at Flat time duration:

$$ECG_{Flat}(i) = ECG\left[(n(T_{Flat}(i)) - \frac{S\_pt}{2} \ldots (n(T_{Flat}(i)) + \frac{S\_pt}{2}\right]$$

c. Compute $ECG_{Flat}(i)$ frequency domain data via Fast Fourier Transform (FFT), and defined as $FFT_{Flat}(i)$. From $FFT_{Flat}(i)$ distribution, we can figure out the difference of the pain between pain or no pain.
d. Keep the effective data from -F_cut to F_cut, a constant value of samples points.

$$FFT_{Flat}(i) = \begin{cases} FFT_{Flat}(i); & -F_{Cut} < f < F_{cut} \\ 0; & \text{otherwise} \end{cases}$$

e. $FFT_{Flat}(i)$ absolute value means the energy at that occurrence time

The Fast Fourier Transform of ECG and labeled as $FFT_{Flat}(i)$ was shown in FIG. 4.

f. Anoval Statistics Test
p=Anoval(|$FFT_{peak}(i)$|; |$FFT_{Flat}(i)$|, Class)
As shown in FIG. 4, the signals were divided into two groups, the p value was less than 0.05.

2.3 Establish the Final Model and Threshold Value

FFT(k) indicates a continuous ECG Data and its period samples are S_pt. In order to enhance the feature of FFT(k) distribution, we do the first order differential as FFT'(k). Compare the FFT'(k) and $FFT'_{Flat}(k)$, to get a pain index g(k), where the α can be set by the subject's pain personal sensation:

$$g(k) = \frac{(|FFT'(k)| - |FFT'_{Flat}(i)|)}{a * std(FFT'_{Flat}(i))} * 100\%$$

$$\text{Judgement Function: }(k) = \begin{cases} X, & g(k_i) > g_{ratio}; 0 < g < f_{low} \\ & \sum(g(k_i) > g_{normal}) \text{ in all } f \\ Y, & \text{otherwise} \end{cases}$$

wherein X and Y are defined as "pain" and "non-pain" respectively; and wherein $g_{ratio}$ and $g_{normal}$ threshold value can be easily set from each maternity history records.

In one example of the invention, the values of X and Y are defined as 0 and 1 respectively, representing "pain" and "non-pain." In another example of the invention, the measurement of pain may be used by more than two values. For example, the values X and Y are defined as being 5 (most pain) and 0 (non-pain) respectively, so that the extent of pain may be represented as 5 (most pain), 4 (more pain), 3 (medial pain), 2 (less pain), 1 (lesser pain) and 0 (non-pain).

In one embodiment of the invention, the ECG data showing a peak profile (Peak) and a flat profile (Flat) was shown in FIG. 5, including the ECG at Flat uterine contraction test data (Upper graph) and ECG at Peak uterine contraction test data (Lower graph).

2.4 Four Maternities Test Results

Case 1

The Peak and Flat original FFT accumulation result were shown in FIG. 6, including Flat FFT data as shown in red and Peak FFT data as shown in blue. The Peak and Flat FFT original mean value distribution were shown in FIG. 7.

The Anova statistics analysis was done for Case 1, $p=1.7961 \times 10^{-47}$. A comparison between the Peak and Flat data in Case 1 is given in FIG. 8.

Case 2

The Peak and Flat original FFT accumulation result were shown in FIG. 9, including the Flat FFT data as shown in red and Peak FFT data as shown in blue. The Peak and Flat FFT original mean value distribution were shown in FIG. 10.

The Anova statistics analysis was done for Case 2, $p=6.81633 \times 10^{-132}$. A comparison between the Peak and Flat data in Case 2 is given in FIG. 11.

Case 3

The Peak and Flat original FFT accumulation result were shown in FIG. 12, including the Flat FFT data as shown in red and Peak FFT data as shown in blue. The Peak and Flat FFT original mean value distribution were shown in FIG. 13.

The Anova statistics analysis was done for Case 3, $p=3.86697 \times 10^{-31}$. A comparison between the Peak and Flat data in Case 3 is given in FIG. 14.

Case 4

The Peak and Flat original FFT accumulation result were shown in FIG. 15, including the Flat FFT data as shown in red and Peak FFT data as shown in blue. The Peak and Flat FFT original mean value distribution were shown in FIG. 16.

The Anova statistics analysis was done for Case 4, $p=0$. A comparison between the Peak and Flat data in Case 4 is given in FIG. 17.

Real-time detect patient's pain signal via continue ECG Data

We continuously collect ECG Data from the machine. Each S_pt period data can transfer ECG Data from time domain into frequency domain. We can gain a pain index to estimate patient's pain level. In the practical application, we can set S_pt/2 to be the cycle of monitor rate.

For example, we set the S_pt=10240 to be period data in each computation samples and the sample rate of heart rate monitor is 512 Hz. Therefore, we can set the cycle is S_pt/2=5120, it means that calculate the pain trend in 10 sec. This parameter needs to satisfy the enough heart rate ECG samples and not too long observed time at the same duration. From comparison of Peak and Flat result in g(k), we can easily set the $g_{ratio}$ and alpha value, usually we can set $g_{ratio}$=1.5, alpha=1.

FIG. 18 showing the uterine contraction of Maternity, FIG. 19 shows the analysis results; wherein the point pt_4 is the time "12:04:30" and the end of point pt_13 is the time; wherein a period ECG data is given and the pain of Maternity is predicted from 12:04:00~12:10:00, cycle=10 sec; $g_{ratio}$=1.5, Alpha=1.

The results of some more cases are provided in FIGS. 20-23: FIG. 20 shows the case of No. 0512 maternity's Anova statistics analysis result, $p=6.81633 \times 10^{-132}$, wherein the point pt_12 is the time "12:06:00," the point pt_26 is the time "12:08:10" and the end of point pt_33 is the time "12:09:20." FIG. 21 provides a comparison between the Peak data and Flat data in the case of No. 0512 maternity. FIG. 22 shows the case of No. 0714 maternity's Anova statistics analysis result, $p=0$. FIG. 23 provides a comparison between the Peak data and Flat data in the case No. 0714 maternity.

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment. Conversely, various features that are described in the context of a single embodiment or example can also be implemented in multiple embodiments or examples separately or in any appropriate suitable sub-combination.

What is claimed is:

1. A system for management of pain in a subject, comprising:
    a system for real-time detection of pain in the subject, which comprises:
        a means for acquiring heart-related biomedical signals in the subject;
        a computing means for transforming the acquired heart-related biomedical signals during a given period of time into signal data for measurement of pain by performing frequency domain conversion for each given period of time of heart-related biomedical signals to form frequency domain signal data, and analyzing the frequency domain signal data in relation to pre-determined modeled data having relationship between frequency domain heart-related signals and pain, wherein the pre-determined modeled data includes at least a pain model which is defined by a peak-shaped profile in frequency domain data and a non-pain model which is defined by flat profile in frequency domain data, generating an index of pain using the results of the analysis, and determining a pain status of the subject based on the index of pain; and
        a display showing the pain status of the subject, and an analgesia system for delivering an analgesic agent,
    wherein the analgesia system is configured to automatically deliver the analgesic agent to the subject based on the pain status and the index of pain.

2. The system for management of pain of claim 1, wherein the heart-related biomedical signals include signals of heart rate (HR), pulse rate (PR), heart rate variability (HRV), and electrocardiogram (ECG).

3. The system for management of pain of claim 2, wherein the heart-related biomedical signals are from the electrocardiogram (ECG).

4. The system for management of pain of claim 1, further comprising:
a means for communication between the system for real-time detection of pain and the analgesia system.

5. The system for management of pain system of claim 1, wherein the analgesia system is provided for administration of acting intravenous, transdermal, transmucosal, or intramuscular analgesia.

6. A method for management of pain in a subject, comprising:
acquiring heart-related biomedical signals in said subject,
transforming the acquired heart-related biomedical signals during a given period of time into signal data for measurement of pain by performing frequency domain conversion for each given period of time of heart-related biomedical signals to form frequency domain signal data,
analyzing the frequency domain signal data in relation to pre-determined modeled data having relationship between frequency domain heart-related signals and pain, wherein the pre-determined modeled data includes at least a pain model which is defined by a peak-shaped profile in frequency domain data and a non-pain model which is defined by a flat profile in frequency domain data, generating an index of pain using the results of the analysis, and determining a pain status of the subject based on the index of pain, and
delivering an analgesic agent to the subject based on the pain status and the index of pain.

7. The method of claim 6, wherein the heart-related biomedical signals include signals of heart rate (HR), pulse rate (PR), heart rate variability (HRV), and electrocardiogram (ECG).

8. The method of claim 7, wherein the heart-related biomedical signals are from the electrocardiogram (ECG).

9. The method of claim 8, wherein the transforming includes deriving a first differential fast Fourier transform (FFT') of the ECG acquired heart-related biomedical to form the frequency domain signal data,
wherein analyzing the frequency domain signal data in relation to pre-determined modeled data having relationship between frequency domain heart-related signals and pain includes FFT's model data, and
wherein the index of pain g(k) is generating using the following formula:

$$g(k) = \frac{(|FFT'(k)| - |FFT_{Flat}(i)|)}{\alpha * std(FFT'_{Flat}(i))} * 100\%$$

wherein FFT'(k) is the first differential fast Fourier transform of the ECG for each given period of time, FFT'$_{Flat}$(i) is the FFT' data of the non-pain model and α is a settable patient pains sensation constant.

* * * * *